United States Patent
Beisel

Patent Number: 5,947,940
Date of Patent: Sep. 7, 1999

[54] CATHETER REINFORCED TO PREVENT LUMINAL COLLAPSE AND TENSILE FAILURE THEREOF

[76] Inventor: Robert F. Beisel, 150 South Mountain Rd., Robesonia, Pa. 19551

[21] Appl. No.: 08/880,619

[22] Filed: Jun. 23, 1997

[51] Int. Cl.$^6$ ................................................. A61M 25/00
[52] U.S. Cl. ......................................... 604/282; 604/264
[58] Field of Search .................................... 604/282, 280, 604/264; 138/123, 124

[56] References Cited

U.S. PATENT DOCUMENTS

| | | |
|---|---|---|
| 3,416,531 | 12/1968 | Edwards . |
| 3,757,768 | 9/1973 | Kline . |
| 3,879,516 | 4/1975 | Wolvek . |
| 3,924,632 | 12/1975 | Cook . |
| 4,044,765 | 8/1977 | Kline . |
| 4,385,635 | 5/1983 | Ruiz . |
| 4,516,972 | 5/1985 | Samson ................................... 604/282 |
| 4,563,181 | 1/1986 | Wijayarathna et al. . |
| 4,737,153 | 4/1988 | Shimamura et al. . |
| 4,863,442 | 9/1989 | DeMello et al. . |
| 4,955,862 | 9/1990 | Sepetka . |
| 4,985,022 | 1/1991 | Fearnot et al. . |
| 5,019,057 | 5/1991 | Truckai . |
| 5,069,674 | 12/1991 | Fearnot et al. ........................... 604/282 |

(List continued on next page.)

FOREIGN PATENT DOCUMENTS

| | | |
|---|---|---|
| 0594201 | 4/1994 | European Pat. Off. . |
| 0596172 | 5/1994 | European Pat. Off. . |
| 2221396 | 7/1990 | United Kingdom . |
| 9616690 | 6/1996 | WIPO . |

OTHER PUBLICATIONS de Jong et al., "A Comparison of Epidural Catheters with or Without Subcutaneous Injection Ports for Treatment of Cancer Pain", *Anesth Analg,* vol. 78, pp. 94–100 (1994).

Rolbin et al., "A Comparison of Two Types of Epidural Catheters", *Can J Anaesth,* vol. 34:5, pp. 459–461 (1987).

Edell et al. "Catheters for Neural Blockade: Materials and Designs", *Techniques in Regional Anesthesia and Pain Management,* vol. 2, num. 2, pp. 103–110 (1998).

Osaki et al., "Advances in Epidural Catheter Designs: A Comparative Study", *AANA Journal,* vol. 64, p. 447 (1996).

Power et al., "Differential Flow From Multihole Epidural Catheters", *Anaesthesia,* vol. 43, pp. 876–878 (1988).

Beck et al., "Epidural Catheters of the Multi–Orifice Type: Dangers and Complications", *Acta Anaesthesiol Scand,* vol. 30, pp. 549–555 (1986).

Morrison et al., "Comparison of Complications Associated With Single–Holed and Multi–Holed Extradural Catheters", *British Journal of Anaesthesia,* vol. 64, pp. 183–185 (1990).

(List continued on next page.)

*Primary Examiner*—Corrine McDermott
*Assistant Examiner*—Cris L. Rodriguez
*Attorney, Agent, or Firm*—Charles A. Wilkinson; Harris A. Wolin

[57] ABSTRACT

A catheter reinforced to prevent luminal collapse and tensile failure thereof, comprising an elongated tubular member having a proximal end, a distal end and a longitudinal extent, the elongated tubular member defining at least one lumen therethrough for enabling fluid flow between the proximal end and at least one opening defined in at least one of the distal end and the elongated tubular member proximal to the distal end thereof; the elongated tubular member including an outer tubular cover and at least one helical reinforcing member for reinforcing the outer tubular cover to prevent radial collapse of the outer tubular cover during being and pinching of the elongated tubular member and to prevent longitudinal breakage of the outer tubular cover under tension, the at least one helical reinforcing member having an unwound length and a wound length, said at least one helical reinforcing member being wound around the longitudinal axis of said elongated tubular member with a length ratio LR less than one (1) plus the approximate ultimate strain of said outer tubular cover where LR equals the unwound length of said at least one helical reinforcing member relative to said wound length of said at least one helical reinforcing member.

19 Claims, 5 Drawing Sheets

U.S. PATENT DOCUMENTS

| | | |
|---|---|---|
| 5,078,702 | 1/1992 | Pomeranz . |
| 5,147,315 | 9/1992 | Weber . |
| 5,176,660 | 1/1993 | Truckai . |
| 5,178,158 | 1/1993 | deToledo . |
| 5,221,255 | 6/1993 | Mahurkar et al. . |
| 5,454,795 | 10/1995 | Samson . |
| 5,538,513 | 7/1996 | Okajima ................................... 604/282 |
| 5,630,806 | 5/1997 | Inagaki et al. ........................... 604/282 |
| 5,695,483 | 12/1997 | Samson ................................... 604/282 |
| 5,702,373 | 12/1997 | Samson . |
| 5,704,926 | 1/1998 | Sutton ..................................... 604/282 |
| 5,776,115 | 7/1998 | Antoshkiw et al. . |
| 5,782,809 | 7/1998 | Umeno et al. ........................... 604/280 |
| 5,782,811 | 7/1998 | Samson et al. .......................... 604/282 |
| 5,792,124 | 8/1998 | Horrigan et al. . |
| 5,792,401 | 8/1998 | Burnham . |
| 5,800,407 | 9/1998 | Eldor . |

OTHER PUBLICATIONS

Michael et al., "A Comparison Between Open–End (Single Hole) and Closed–End (Three Lateral Holes) Epidural Catheters", *Anaesthesia,* vol. 44, pp. 578–580 (1989).

Cragg Convertible Wire™ new product bulletin from Medi–Tech.

(PITCH INCREASES AS ELASTOMERIC TUBE IS STRETCH L→L (1 +ε))

Assuming Monofilament To Be Extensible:

$$\pi^2 D^2(\varepsilon) + P^2(1+\varepsilon)^2 = H^2 = \text{Constant}$$

Initial Diameter $D^2 = \dfrac{H^2 - P^2}{\pi^2}$ $$D^2(\varepsilon) = D^2 - \dfrac{2\varepsilon P^2}{\pi^2} - \dfrac{\varepsilon^2 P^2}{\pi^2}$$

Define Diameter Ratio $\equiv \dfrac{D(\varepsilon)}{D} = \left[ 1 - \dfrac{P^2}{\pi^2 D^2}(\varepsilon^2 + 2\varepsilon) \right]^{1/2}$ Define Length Ratio $\equiv LR = \dfrac{H}{P} = \left(1 + \dfrac{\pi^2 D^2}{P^2}\right)^{1/2} = \left(1 + TAN^2 \Theta\right)^{1/2}$ $$\dfrac{D(\varepsilon)}{D} = \left[1 - \left(\dfrac{1}{LR^2 - 1}\right)(\varepsilon^2 + 2\varepsilon)\right]^{1/2} = \left[\dfrac{LR^2 - (1+\varepsilon)^2}{LR^2 - 1}\right]^{1/2}$$

For a Fluid Tube of Poisson Ratio 0.5 $\dfrac{D(\varepsilon)}{D} = \left(\dfrac{1}{1+\varepsilon}\right)^{1/2}$ Note: $D(\varepsilon) \to 0$ (Coil is Taught) At $\varepsilon = LR - 1$

CATHETER REINFORCED TO PREVENT LUMINAL COLLAPSE AND TENSILE FAILURE THEREOF

FIELD OF THE INVENTION

This invention relates generally to medical catheters, and in particular, to a small diameter catheter with a helical reinforcing structure that provides kink resistance and enhanced longitudinal strength without undesirably increasing flexural stiffness.

BACKGROUND OF THE INVENTION

The use of catheters for site-specific, transcutaneous introduction of diagnostic and therapeutic agents or devices is well known in many medical arts. The many different applications of such catheters sometimes require construction from materials having specialized physical properties and configurations which dictate various construction methods and/or material selection.

Common catheter requirements include the incorporation of a proximal portion that is longitudinally incompressible to enable the catheter to be pushed through a needle or introducer device, or over some type of guiding wire. In this connection, it must have a minimum column strength, either inherently by virtue of the material stiffness of the catheter tubing or from binding together helical wraps in opposing directions, as a result of a reinforcing coil contained within the catheter tubing having initial tension, or imparted to the catheter tubing from a stylet inserted therein. Next, it is desirable to have a highly flexible distal end (i.e., a "soft tip") to minimize the risk of patient injury during catheter insertion and to allow the catheter to advance into tortuous paths. The catheter should have adequate reinforcement to prevent kinking as a result of bending or luminal collapse under radial compression from any fluid path connectors or adapters. Furthermore, the catheter should be designed with as thin a wall as practicable, yet in a manner to maximize tensile strength with minimal tensile compliance to allow controlled withdrawal. It should exhibit radioopacity and be devoid of any long, continuous conductive wires (even simply diamagnetic or paramagnetic materials) contraindicated in MRI procedures.

If a catheter must be manipulated and steered during bodily insertion into relatively long, tortuous paths, it must possess good torsional stiffness along its length and preferably have a relatively lubricious external surface. However, for applications where the insertion path is relatively short, through an epidural needle for example, or where blood flow tends to direct the catheter as in the case of peripherally inserted central venous catheters (PICC catheters), such torsional stiffness is unnecessary. Strong pinching, as can occur with an epidural catheter by the ligamentum flavum and vertebrae, may also place an upper limit on the coefficient of friction which will still allow withdrawal. If the catheter is to be advanced over a guiding wire, an internal surface with a low coefficient of friction is sometimes required. This is achieved by employing either a fluoropolymeric, hydrophillic, or otherwise lubricious coating, or a hard, roughened internal surface that minimizes actual contact area.

When a catheter must enable high rates of injection, the ability to withstand internal pressures of several hundred psi may be required, especially in the proximal region where pressure is highest. Optical transparency may be advantageous in evidencing vascular placement or assuring non-vascular placement. Such transparency is seldom disadvantageous.

The progressive miniaturization of catheters has reached a point in development where the requirements for thin walls, large I.D.'s, good tensile strength, and kink-resistance make using a soft material problematic. There is a need, for example, for a 2 French (⅔ mm O.D.) PICC catheter made from soft silicone or polyurethane. Yet the longitudinal strength of such a small, soft, atraumatic catheter is dangerously low.

Small, soft-tip epidural catheters have even more rigorous requirements. After such a catheter is inserted and the epidural needle is withdrawn over it, a fluid fitting is applied to the catheter's proximal end and achieves a fluid-tight seal by firmly compressing an elastomeric sleeve against the catheter's surface. This compressive force can cause radial collapse. Pinching of the catheter can also occur between vertebrae of an erect spine. The catheter must resist these compressive forces without compromising patency. It must also resist kinking and remain flexible, even when bent sharply.

To enable the catheter to be reliably removed from a tight vertebral pinch without breaking, high tensile strength is required. Despite the best efforts in the industry, breakage of these catheters is an ongoing problem, especially with catheters made of softer, usually tackier materials. The use of a slippery material or coating to reduce the removal force is inappropriate since a lower coefficient of friction also potentiates catheter migration and reduces the force required to remove the compression fitted adapter from the proximal end of the catheter. The reliable function of Tuohy-Borst compression adapters and the like with conventional epidural catheters is already problematic with only a fine line dividing easy removal due to inadequate compression and luminal collapse from excessive tightening.

Although polyamide and hard polyurethane tubing satisfy these requirements, they have a relatively thick wall and, as a consequence, are relatively stiff, causing an unnecessarily high incidence of venous cannulation, paresthesiae, and, in a small number of incidents, permanent nerve damage. In a study conducted by Stephen H. Rolbin, "A comparison of two types of epidural catheters," then recent data from Mount Sinai Hospital, Toronto documented "a 30 per cent incidence of paresthesiae and a 10 per cent incidence of blood returning after insertion of the epidural catheter." *Can J Anaesth* 1987, Vol 34, No. 5, pp 459–61. The latter problem is especially serious, as inadvertent intravenous injection of the bolus of anesthetic can induce convulsions, hypotension, and loss of consciousness. His paper goes on to report the superior performance of a polyurethane catheter, reported as "much softer than the one made of nylon," which lowered the incidence of paresthesiae from 44 to 24 per cent and that of blood vessel trauma from 12 to 6.7 per cent. The required resistance to compressive collapse and pinching, however, obviously limits the extent to which softening an unsupported tube can be relied on to reduce trauma. In fact, occlusive kinking of a softer polyurethane catheter was noted by P. de Long and P. Kansen, as a problem occurring near connections to implanted injection ports. "A Comparison of Epidural Catheters With or Without Subcutaneous Injection Ports for Treatment of Cancer Pain," *Anest. Analg.* 1994, 78: 94–100. Studies have since shown a dramatic and useful further reduction of paresthesiae and blood aspiration when using even softer, coil reinforced epidural catheters.

An early radially reinforced soft-tip epidural catheter known as the THERACATH was introduced by Arrow International, Inc. ("Arrow") in 1985. It used a polyolefin heat shrink tube to encapsulate a close-wound 0.004" stainless steel spring wire with an axial safety ribbon to provide several pounds of tensile strength. The 0.004" wall polyolefin tube possessed a relatively low coefficient of friction. However, the relatively high cost attributable to the spring wire, with its double welded safety ribbon and opened distal coils largely precluded widespread use of the product.

The Arrow FLEXTIP dual-durometer epidural was introduced in 1989. It consisted of several inches of 93 Shore A polyurethane tubing, 0.5 mm (0.020") I.D. and 1.0 mm (0.040") O.D. butt welded to several feet of a stiffer polyurethane tube of identical dimensions. While the stiff proximal portion, of the epidural provided compressive strength adequate to support the compression fitting and to provide vertebral pinch resistance, the soft tip had, by virtue of its relatively thick wall, sufficient kink resistance to remain patent in the epidural space.

The Arrow FLEXTIP PLUS epidural catheter was developed in early 1992. A fabrication method of applying a continuous polyurethane coating around a relatively simple spring coil allowed many of the advantages inherent in the FLEXTIP dual-durometer epidural to be reproduced. The FLEXTIP PLUS has been widely praised by the medical profession and has been successful in the marketplace. The relatively high strength and abrasion resistance of the continuous polyurethane tube gives the catheter good tensile integrity. Nonetheless, there are some shortcomings in its design and use. Although the stainless steel coil, wound with initial tension, provides enough column strength for many anesthesiologists to insert the catheter without a stiffening stylet, it has several disadvantages. Notwithstanding the fact that the stainless steel coil provides more than adequate support against kinking and radial compression, it does not add significantly of the tensile strength to the catheter because it has no safety ribbon welded at the ends and is close-wound from 0.004" wire with a large length ratio, LR. The catheter therefore derives almost all of its tensile strength from the polyurethane coating alone. The column strength provided by the coil is judged by some to provide inadequate stiffness for catheter insertion. Furthermore, the initial tension, close-wound metal coil results in a catheter that is opaque throughout its longitudinal extent except for two "semi-transparent" flashback windows where the coil has been stretched. The presence of the metal coil also precludes use of such catheters in MRI procedures. Even though the extremely weak ferromagnetic character of the cold-worked austenitic stainless steel wire minimizes concerns over inductive heating or over forces on the catheter in magnetic field gradients, the long, continuous conductor, if allowed to lie straight along the magnet axis and against the bore of the magnet could develop high induced voltages. Though the discussion over the relative advantages of single orifice end-hole as compared to multi-orifice side-hole epidural catheters continues, there appears to be a market preference for side-hole catheters. One safety concern raised by some about side-hole epidurals involves a scenario where the catheter tip has penetrated an epidural vein so as to position the distal side-hole intravascularly while the more proximal holes remain extravascular. Low pressure injections tend to emerge from only the proximal holes, while high pressure injections flow from all openings. Given this, some postulate a hazard with side-hole catheters when aspiration and low pressure test dose does not detect a partial vascular placement, revealed suddenly later by systemic effects of a high pressure top-up dose. Inasmuch as the likelihood of vascular penetration by a soft-tip epidural is much less likely than for earlier, conventional catheters, the risk of using a soft-tip side-hole epidural can be argued to be minimal. The presence of a metal coil within the FLEXTIP PLUS, however, complicates the construction of a version where the distal end is closed and fluid is emitted through a plurality of orifices in the wall of the catheter near the distal tip. It is impossible to terminate the coil short of the side-holes, since the unsupported thin polyurethane tube would then kink or collapse and occlude. Perforation of the coating significantly reduces the strength of the catheter at that point and potentiates breakage of the tip during removal. Many anesthesiologists prefer side-hole catheters despite this and earlier mentioned risks and notwithstanding the facts that slight local tip weakness plagues all current side-hole catheters and clinical studies have shown no difference in analgesic efficacy between side-hole and end-hole catheters. They cite concern over one sided blocks caused by anesthetic jetting laterally from an end-hole catheter which is almost never oriented perfectly parallel to the spinal axis.

The cost to manufacture the Arrow FLEXTIP PLUS has been reduced to a level which allows the product to sell for only about 30% more than conventional catheters. Notwithstanding praiseworthy success in dramatically reducing paresthesiae and venous cannulation, some suggest that the FLEXTIP PLUS remains cost-ineffective. The need for improved properties at essentially no increase in cost is especially significant in the international markets where developing economies cannot bear any cost premium.

Use of helical reinforcement in catheters is far from unique in the field as evidenced by the following prior art.

U.S. Pat. No. 3,416,531 to Edwards discloses braiding a monofilament material such as metal, nylon, or teflon in opposite spiral directions into the wall of a tube in order to provide the tube with enhanced torsional stiffness without greatly increasing flexural stiffness. The presence of helical wraps in both directions, though providing torsional stiffness, requires the reinforcement to have one-half the thickness which would be possible for a non-crossing spiral wrap in only one direction. This reduces the moment of inertia of the ribbon's cross section by a factor or eight and results in a net four-fold decrease in kink resistance. Braiding is therefore a poor approach when resistance to kinking is paramount and torsional stiffness is unimportant.

U.S. Pat. Nos. 3,757,768 and 4,044,765 to Kline disclose the use of a stainless steel helical coil spring to reinforce a flexible intravenous feeding tube formed from solvent-cast polymer.

U.S. Pat. No. 3,879,516 to Wolvek teaches the use of a spiral filament of polyurethane or other solvent soluble and hence bondable material to provide integral reinforcement within a relatively thin walled catheter to provide kink-resistance. No mention is made of longitudinal strength, diameter, pitch or helix angle.

U.S. Pat. No. 3,924,632 to Cook teaches the use of fiber glass braided into the wall of a catheter to provide torsional stiffness.

U.S. Pat. No. 4,385,635 to Ruiz teaches a soft tipped angiographic catheter employing a central polyamide reinforcing tube inside a softer elastomeric sleeve. By tapering the wall thickness of the polyamide to zero within 1–7 mm of the distal end, the tip consists only of the softer urethane and is therefore itself soft.

U.S. Pat. No. 4,563,181 assigned to Mallinckrodt, Inc., discloses a soft tip intravascular catheter wherein the tip made of a nylon blend is fused or welded at a butt joint to the tubular body made of a different, stiffer nylon.

U.S. Pat. No. 4,737,153 to Shimamura et al describes a flexible, kink-resistant therapeutic tube reinforced by a spirally embedded reinforcing material. In addition to steel, stainless steel, or tungsten wire, numerous synthetic fibers, protein fibers and carbon fibers are also mentioned as candidate reinforcing materials.

U.S. Pat. No. 4,863,442 to DeMello teaches the construction of a soft tip catheter having a wire-braided teflon core and polyurethane jacket. The soft tip consists of approximately two (2) mm of polyurethane bonded to the braided core of the catheter.

U.S. Pat. No. 4,955,862 to Sepetka teaches a catheter which includes a flexible distal segment comprised of a flexible outer tube and a low-friction distal segment comprised of a flexible outer tube and a low-friction surface structure embedded in the polymer tube so as to form hard, disjoint internal surface regions. These hard surface regions are provided by the windings of a helical coil of metal or hard-surfaced polymer, and are intended to provide a low friction, small contact area to enable the catheter to be introduced over a guide wire through a tortuous path or to enable a guide wire to be passed through and manipulated within the catheter with relatively low forces.

U.S. Pat. No. 4,985,022 to Fearnot discloses a catheter having both durable proximal and flexible distal segments. The durable segment consists of a stainless steel cannula, rendered kink resistant by an external spiral wrapping with round or flat wire or by helical grooving of the outer diameter. The distal flexible segment is formed by a plastic tube surrounded by a tightly coupled wire coil. The catheter can be made with either an end hole or, by blocking the end of the wire coil and slitting the plastic tube, side exit of the medication can be allowed through the windings of the coil. Though allowing high pressure injection through a catheter of very small diameter, the complexity of the structure deems the devices far too expensive for general use.

U.S. Pat. No. 5,019,057 to Truckai discloses a flexible catheter comprising at least one tubular layer within a tubular sheath of helically crossing strands, at least one of which has a width that is four (4) to eight (8) times greater than its height and at least one of which is circular in cross section. The reinforcing strands are either mechanically retained between resilient tubular layers bound to one another, or can be coated with primer to improve their adhesion to the respective tubular layers. The braided reinforcing filaments may be made of a biaxially oriented thermoplastic material. The various embodiments of the Truckai invention are intended to exhibit increased longitudinal and torsional stiffness. However, no mention is made of longitudinal strength or specific helical angles.

U.S. Pat. No. 5,069,674 to Fearnot teaches a small diameter epidural catheter which is both flexible and kink-resistant. Positioned within the lumen of a tubular sheath (0.025–0.075 mm, 0.001–0.003" wall) of high tensile and flexural strength material, is a spirally wound coil of either hardened stainless steel (0.025–0.075 mm, 0.001–0.003" diameter), other metals or alloys, carbon filaments, hard plastic fibers or combinations thereof. A safety wire affixed to both ends, either laying within the catheter lumen or wrapped helically around the reinforcing coil, prevents stretching of the wire coil. When flexed or bent, the coils move within the lumen of the tube to distribute forces along the surface of the bent tube. Fearnot teaches a tightly wound coil at all but the distal end with a coil diameter ratio (coil diameter/wire diameter) of 4–10.

U.S. Pat. No. 5,078,702 to Pomeranz discloses a soft tip catheter having an inner sheath made of a rigid polymer. The stiffer proximal portion has a braid embedded between inner and outer sheaths, while the soft, distal tip lacks this stiffening braid. The compatibility of the inner and outer polymeric materials and the continuity of the inner sheath improves tensile integrity.

U.S. Pat. No. 5,147,315 to Weber teaches an access catheter for the female reproductive system having a segment which resists constriction by virtue of a reinforcing metal coil embedded between inner and outer tubular layers. A coil geometry suggested is 0.025 mm×0.125 mm (0.001"×0.005") ribbon wound with a 0.9 mm (0.036") I.D. and a 0.1 mm (0.004") gap.

U.S. Pat. No. 5,176,660 to Truckai discloses the same invention as his '057 Patent, with the addition of longitudinally oriented wires well known in the braiding art as "zero angle" or "axial" yarns introduced through hollow horn gear shafts in the braider. The longitudinal stiffness of at least a portion of the catheter is thereby increased. No mention is made of longitudinal strength.

U.S. Pat. No. 5,178,158 to Fernando de Toledo discloses a guidewire-catheter with a soft tip. A stainless steel flat wire coil provides kink-resistance to two concentric tubes, one of which is made from polyimide extending to within a short distance of the distal tip, and one of which is heat shrunk teflon covering the entire length of the catheter and independently forming the soft, distal tip. A removable core wire allows the device to function first as a guide wire and, upon removal of the core wire, as a catheter. The polyimide sheath imparts strength to the proximal segment.

U.S. Pat. No. 5,221,255 to Mahurkar et al teaches the construction of a reinforced multiple lumen catheter employing a heavy straight reinforcing strip between two D-shaped lumens to transfer force from the proximal end of the soft silicone catheter to the distal end during insertion. It employs a spiral embedded in the catheter wall to minimize kinking. This spiral is preferably made with a thin metal wire or, alternatively, a strong polymeric monofilament.

Another "Kink-Free Spiral-Wound Catheter" is disclosed in U.S. Pat. No. 5,454,795 to Samson, wherein stiffener ribbons, typically metallic, are wound within the catheter to create a catheter having controllable stiffness. "Fibrous materials" including polyaramids (e.g. Kevlar), carbon fibers, and lower performance polymers such as Dacron and the Nylons may be used for reinforcement. Silk and cotton are acceptable natural fibers. It is taught that the preferred manner of using non-metallic ribbons is "in combination with metallic ribbons to allow 'tuning' of the stiffness or as an opposite 'handed' ribbon in the composite to lessen the tendency of the metallic ribbon to unwind." An inner liner may or may not be present. The outer layer is applied by heat shrinking, dipping into a molten polymer bath or into a polymer dissolved in a solid or into a suspension or latex comprising the outer cover polymer, or by spraying the material. However, no mention is made of the required longitudinal strength of the catheters and there is certainly no suggestion of the importance of helical angles or length ratios in regard to this property inasmuch as not a single diameter is specified anywhere in the Patent.

UK Patent Application GB 2,221,396A discloses an epidural catheter closed at the distal end thereof with a plurality of elongate slits or a single helical slit through the wall of the distal end of the tube so as to increase the flexibility of the tip and reduce jetting through an occluded end hole. Though mention is made of an existing wire reinforced, end-hole catheter, an object of the invention is to provide a much lower cost, "non-end-hole" catheter. No mention is made of longitudinal strength.

International Application Number PCT/US95/14865 (WO96/16690) by McWha describes "A Catheter Having Wall Support to Prevent Collapse Thereof." This Application discloses the original concept behind the "New B-D Ribflex" or "Perisafe Ribbed Lumen" epidural catheters which Becton-Dickinson has recently introduced (American Society of Anesthesiologists meeting, New Orleans, November 1996). This reference discusses the importance of a soft epidural catheter to eliminate insertion trauma. The disclosed invention proposes using a metal coil only in the proximal end of the catheter whereupon the adapter element is applied, and structuring the interior of the remaining length of the catheter with longitudinal rib elements to prevent collapsing and/or kinking during use. Such internal ribbing only prevents complete occlusion during kinking and in no way reinforces the tube against collapse.

Despite all the intentions evidenced by the above Application to produce a superior, cost-effective epidural catheter, the "New B-D Ribflex" epidural catheter actually brought to the market has no coil reinforcement anywhere, has only internal ribbing which in no way actually prevents kinking and, lacking any reinforcement, relies on the relatively high hardness of the extrusion to assure its patency. It is in essence another conventional side-hole epidural. Thus, the long-standing problem of producing a low cost, high quality soft-tip epidural catheter remains unsolved.

SUMMARY OF THE INVENTION

In accordance with the foregoing described shortcomings in prior art catheters, it is an object of the present invention to provide a catheter having a reinforced structure that prevents tensile failure and radial collapse thereof during use.

It is a further object of the present invention to provide a catheter having a reinforced structure that has a soft atraumatic tip yet is exceptionally strong and kink-resistant.

It is another object of the present invention to provide a catheter which can be manufactured in either an end-hole or side-hole version.

It is still another object of the present invention to provide a catheter in accordance with the above having translucent characteristics to enable blood flow therethrough to be observed by the physician or other medical personnel.

It is yet another object of the present invention to provide a catheter in accordance with the above that is relatively inexpensive to manufacture.

It is another object of the present invention to provide a catheter in accordance with the above that is suitable for use in Magnetic Resonance Imaging (MRI).

It is still another object of the present invention to provide a catheter in accordance with the above that is safe to use with superior all around performance.

In accordance with the above objects and additional objects that will become apparent hereinafter, the present invention provides a catheter, comprising: an elongated tubular member having a proximal end, a distal end and a longitudinal extent, the elongated tubular member defining at least one lumen therethrough for enabling fluid flow between the proximal end and at least one opening defined in at least one of the distal end and the elongated tubular member proximal to the distal end thereof; the elongated tubular member including an outer tubular cover and at least one helical reinforcing member for reinforcing the outer tubular cover to prevent radial collapse of the outer tubular cover during bending and pinching of the elongated tubular member and to prevent longitudinal breakage of the outer tubular cover under tension, the at least one helical reinforcing member having an unwound length and a wound length, the at least one helical reinforcing member being wound around the longitudinal axis of the elongated tubular member with a length ratio LR less than one (1) plus the approximate ultimate strain of the outer tubular cover, where LR equals the unwound length of the at least one helical reinforcing member relative to the wound length of the at least one helical reinforcing member.

In a preferred embodiment, the length ratio LR is less than approximately seven (7), and is preferably between approximately two (2) and three (3). The prior art practice relative to reinforced catheters typically employs high length ratios in the range of approximately 7–30. The use of low length ratios, less than one (1) plus the ultimate strain of the material from which the outer tubular member is produced in accordance with the present invention, ensures that the catheter outer tubular member does not fail in tension prior to the reinforcing structure.

In the illustrative embodiments, the reinforcing layer is approximately 0.1 to 0.125 mm (0.004"–0.005") thick and approximately 0.023 to 0.3 mm (0.009"–0.012") wide, and is wound from uniaxially oriented flat monofilament spun from materials including polyethylene terephthalate, polybutylene terephthalate, polypropylene, nylon, and other polyesters. Alternatively, the reinforcing material is wound from a reinforcing ribbon produced by slitting extruded and oriented film of materials including polyethylene terephthalate, polybutylene terephthalate, polypropylene, nylon, and other polyesters. If desired, at least one of these helical reinforcing members can be provided with X-ray opacity so as to allow visualization of the catheter under readily accessible fluoroscopy by filling with at least one radioopaque material from a list including barium sulfate, various bismuth compounds and elemental powders of tungsten, tantalum, tin, or platinum. The most effective such filling is 5–20% by volume loading of finely divided tungsten powder, accomplishing radioopacity at both relatively low cost and minimal occupied volume so as to have minimal effect of the physical properties of the reinforcing member. If desired, the elongated tubular member further comprises an inner tubular layer residing inside the outer tubular cover, the helical reinforcing member being disposed between the outer tubular cover and the inner tubular cover. The outer tubular cover and the inner tubular layer may be fabricated from elastomers including silicones, polyether block amide resins, polyurethanes, plasticized polyvinylchlorides, melt processable fluoropolymers, polyester elastomers, styrenic block copolymers, ionomers, acrylic elastomers, and polyolefin elastomers.

In one embodiment of the invention, the outer tubular cover defines a wall thickness and the at least one opening is defined in at least one of the distal end of the outer tubular cover and the elongated tubular member proximal to the distal end thereof through the wall thickness. The at least one opening can be disposed between wraps of the at least one helical reinforcing member. In certain embodiments, multiple wraps of reinforcing members may be wound in accordance with the same arrangement. In those embodiments, at least one of the wraps may be removed from a portion of the elongated tubular member proximal to the distal end thereof and the at least one opening defined between remaining wraps.

In accordance with the foregoing, many other advantages of the present invention will become apparent as the detailed description proceeds below with particular reference to the accompanying drawings.

DETAILED DESCRIPTION OF THE PREFERRED EMBODIMENTS

Figure 1:
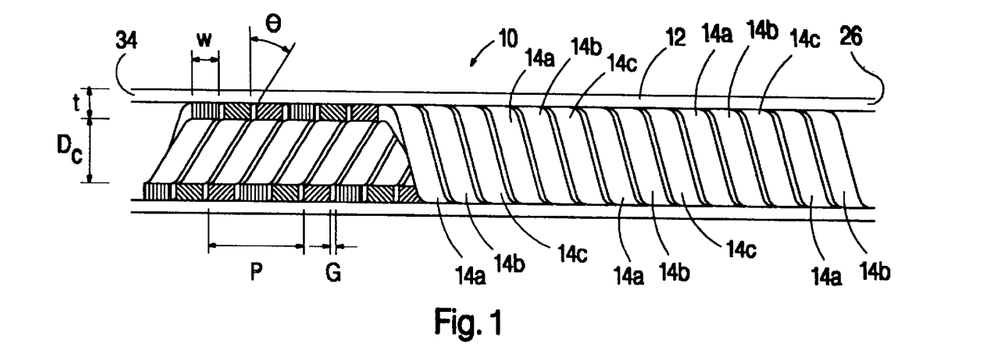
FIG. 1 is a side view of a reinforced catheter in accordance with the present invention shown with the reinforcing coils partially cut away.

Referring now to the several views of the drawings, there is depicted a reinforced catheter generally characterized by the reference numeral 10 and several graphs and mathematical relationships used in optimizing the design. The longitudinal strength, a very important property of an epidural catheter, is mentioned infrequently in the prior art, and has been heretofore derived only from the strength of the tubular structure surrounding the spiral reinforcement or some additional "safety wire" separate and apart from the reinforcing coils. As described above, an object of the current invention is sharing the role of longitudinal strengthening between the tubular layers and the spiral reinforcement so as to allow production of a stronger, thin-walled, highly flexible catheter. This goal relies critically on the geometry of the reinforcing coil and its response to elongations of several hundred per cent. FIG. 1 is a side view of the catheter of the present invention shown with reinforcing coils partially cut away generally comprised of a catheter 10 having an elongated tubular member comprised of an outer tubular cover 12 and at least one helical reinforcing member generally described herein by reference numeral 14, but shown more particularly in FIGS. 1 and 6 by three distinct reinforcing members 14a, 14b and 14 c. In the exemplary embodiment, three helical reinforcing members 14a, 14b, and 14c are used, with less preferred embodiments of the catheter of the invention incorporating one or two reinforcing members, each member used, having a pitch P, core diameter Dc, ribbon thickness t and width w, winding gap G, and helix angle Θ.

It is also useful to introduce the Length Ratio LR of a spiral coil as discussed above. It is simply the length to which a coil of unit length will ultimately stretch before becoming taught, although the coil begins to exert significant Hookean forces before this limit is reached.

Figure 2:
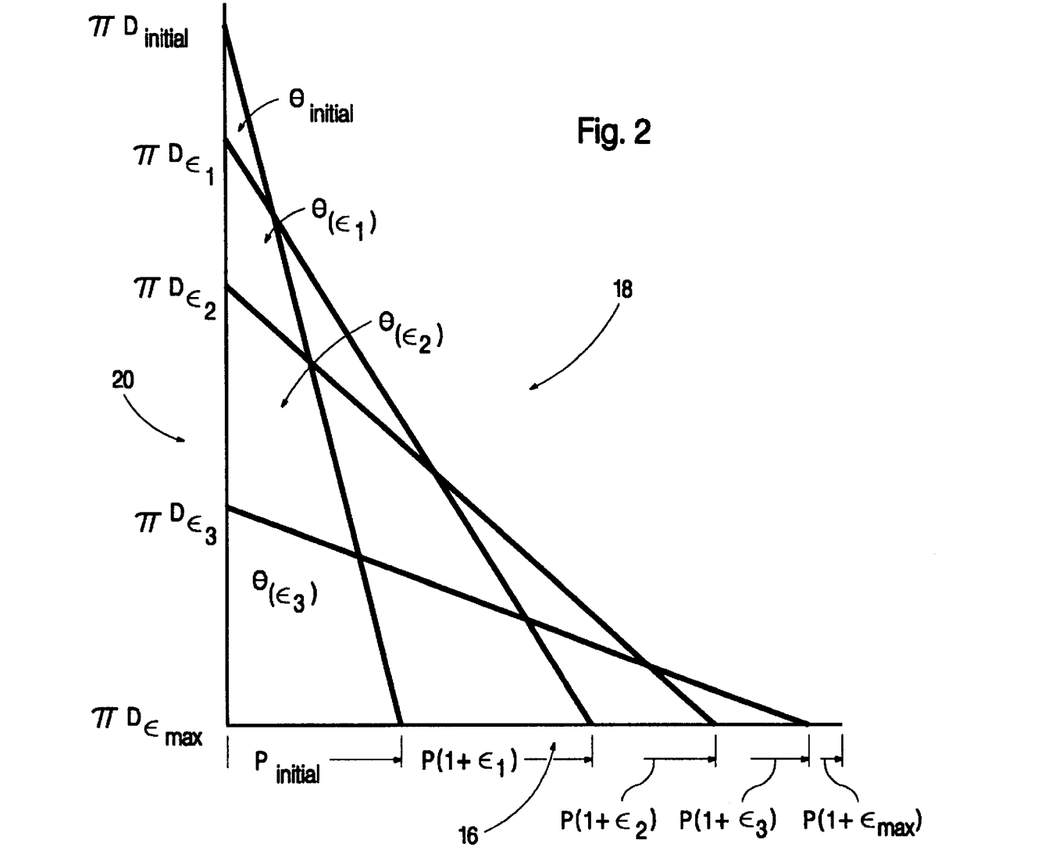
FIG. 2 is a graphical diagram demonstrating the relationship between initial and strained pitch, circumference, diameter and helical length of the reinforcing coils' of the catheter of the present invention.
Figure 3:
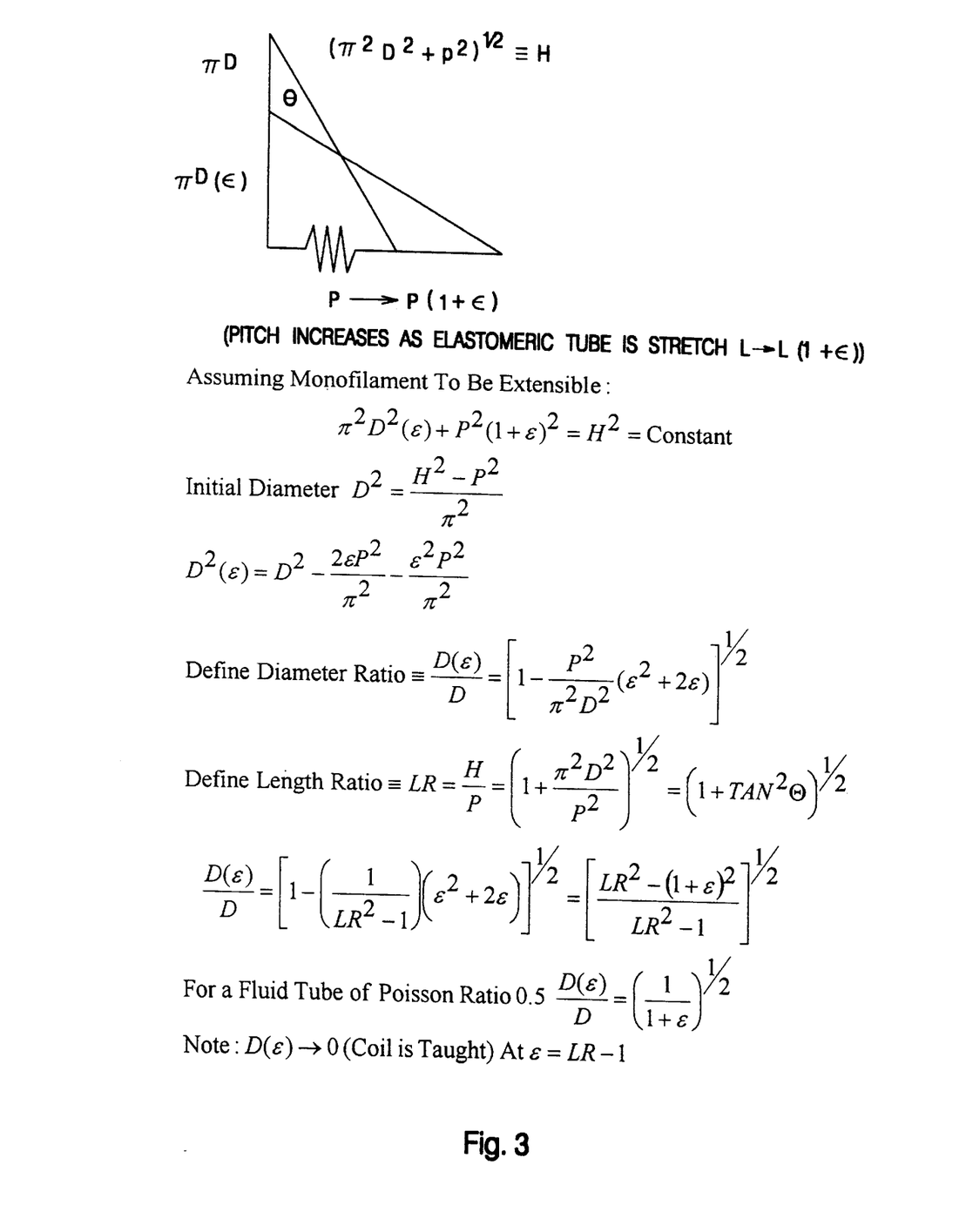
FIG. 3 shows the mathematical relationships graphically demonstrated in FIG. 2.
Figure 4:
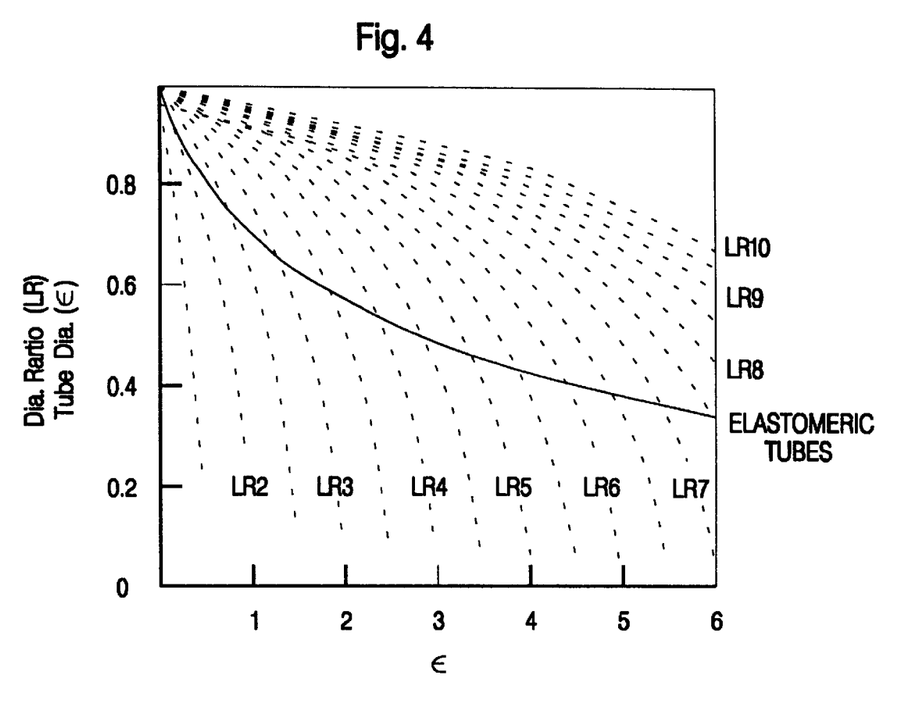
FIGS. 4 and 5 graph the dependence of reinforcing coil diameter on initial length ratio and strain, as well as the diametrical shrinkage of an unsupported elastomeric tube.
Figure 5:
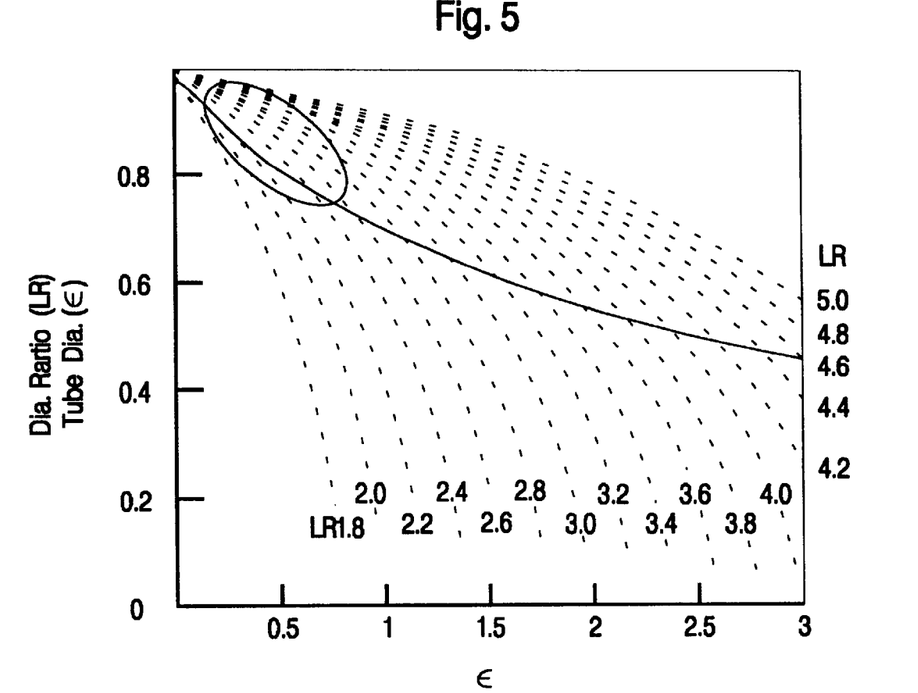

Referring now to FIG. 2, there is shown the simple geometric relationship of the coil geometry on strain, based on the assumed small elongation of the helical reinforcing members themselves resulting from their high tensile modulus which is much greater than the spring rate of the coil. As the horizontal side 16 of the triangle, which represents initial and strained pitch, is elongated by strain, the hypotenuse 18 of the triangle, which represents monofilament length and is assumed to be of constant length, slides down the vertical side 20 of the triangle, which represents decreasing coil circumference, π times diameter D, a function of strain ε going to zero at maximum strain. One skilled in the art can appreciate that coils of small initial Θ have initially a slow diametrical shrinkage with strain and greater total elongation than coils with a large initial Θ, which exhibit a more rapid reduction in coil diameter with strain and tighten after only perhaps doubling in length. FIG. 3 shows the derivation of the mathematical relationship between coil diameter, length ratio LR and strain ε. FIGS. 4 and 5 graphically depict the response of the diameter of coils of various length ratios to elongation as well as the response of the diameter of an unsupported tube of a soft elastomeric material with a Poisson ratio of 0.5 to stretching. The diameter of a tube of real elastomer having a Poisson ratio less than 0.5 would exhibit slower diametrical shrinkage with strain.

If a spiral reinforcement coil 14 is wound with a length ratio LR less than one (1) plus the ultimate strain of the polymeric tubular coating 12 applied to the coil 14, the coil will start to bear the tensile load before that coating fails. Thus, the reinforcing coil 14 and coating 12 operate in concert to prevent tensile failure. With higher LR's, the coating 12 breaks first and the reinforcing coil 14 breaks afterwards—their respective strengths are not additive. Most close-wound coils have high length ratios. For example, the round wire coils specified by Fearnot in the prior art '674 Patent have "diameter ratios" of 4–10, and LR's of 10–28. The flat wire coil suggested by Weber in the '315 Patent has a LR of 13. The coil used in a 20 ga. Arrow FLEXTIP PLUS epidural catheter wound to a diameter of 0.625 mm (0.025") with 0.075 mm×0.25 mm (0.003"×0.010") stainless steel flat-wire has a LR of 7. When reinforcing tubes of, for example, 90 Shore A polyurethane, where longitudinal strength must be maximized and tensile compliance minimized, the ideal length ratio LR is between 2 and 3. Such a length ratio LR not only assures tensile support before the typical ultimate strain of 5–6 of the polyurethane tubular coating 12 is reached, but also matches the diametrical response of the polyurethane tubular coating 12 and the reinforcing member 14 in the range of strain epsilon 0 to 1 that is usually experienced in use (elliptical region in FIG. 5). In this manner, regardless of whether steps have been taken to adhere the reinforcement to or embed it in the tubular coating 12, the reinforcing coil 14 and tubular coating 12 move in concert. When a more compliant catheter is desired, e.g. a soft silicone PICC as shown generally in FIG. 8, a slightly higher LR of between four (4) and five (5) still offers protection against tensile failure while allowing easier stretching of the catheter at small elongations.

Winding coils for reinforcement from flat ribbons of great width to achieve such small length ratios is unacceptable, since the resulting coils are prohibitively stiff. Winding single end reinforcement coils at a long pitch, leaving large gaps between turns in order to achieve a low LR seriously decreases the kink resistance of the catheter and potentiates an unacceptable rippled exterior surface. While winding multifilar (multiple leads) coils of long pitch would restore kink resistance and allow for a smooth surface as the multiple leads "fill in" the structure, coils wound at such long pitches are much stiffer than shorter pitch or unifilar (single lead) coils. Arranging two or three solid metallic coils in parallel multiplies this stiffness to a level which is unacceptably high, though more numerous coils of finer wire or coils wound from multifilament 'wire yarns' would be sufficiently soft. Furthermore, metallic coils from cold-work-hardened metals, as is common, always spring off the mandrel when released. Cold-work-hardened wire cannot be preformed to such small diameters as are needed for epidural and PICC catheters, though preforming to larger diameters is possible. This problem was foreseen by Samson in the teachings of the '795 Patent that non-metallic ribbons are used only in conjunction with metallic ribbons, wound over them in opposite direction to constrain them. An alternative to this physical constraint of cold-worked austenitic stainless steels and the like is the use of wires drawn from metals which can be heat treated so as to set the shape of the wound coil. Various 400 series martensitic stainless steels can be hardened and tempered and Carpenter 455 stainless steel can be age hardened after winding to eliminate spring off. The corrosion resistance of these materials, unless plated, would prove inadequate to withstand the concentrated brine that results when physiological saline within the catheter loses moisture to the atmosphere through the catheter wall. Superelastic nickel-titanium can be shape set after coiling by austenitizing at 400–500 C. Titanium 6A14V ELI could be stress relieved and age hardened after coiling at temperatures between 480 and 600 C. These processes would be rather expensive and obviously preclude use of an inner organic layer within the wound coil. Samson's teaching away from the sole use of non-metallic reinforcing ribbons misses one synergistic advantage of the present invention: The lower transverse stiffness of polymeric ribbons, even when filled with up to 20% by volume finely divided metal, allows the use of multifilar coils wound at small length ratios to produce reinforcing coils which, while providing good radial support, are still very flexible and which can be heat set, even when wound over an inner tubular layer, to avoid spring-off and twisting upon core removal. Whether metallic or non-metallic, the multiplicity of ends allowed and the smooth coils produced at these low LR's are much stronger than their single end counterparts and enjoy the important characteristic of strengthening the catheter 10 by tightening before the thin, soft tubular cover 12 of the catheter 10 breaks.

The use of flat non-metallic monofilament in many cases allows thermal shape-setting and direct overextrusion of the wound cores without the problems of "spring off" encountered when using some metallic reinforcement. Some metallic components cannot be preformed to the required small diameters and must be either braided, with resulting loss of kink-resistance, or otherwise constrained to allow extrusive coating. Use of 'shape-set' metallic reinforcement has the disadvantages of relatively high cost, optical and opacity, electrical conductivity.

As shown generally in FIG. 6, catheter construction in continuous lengths begins by winding the helical reinforcing coil 14 upon a core 24 which is subsequently removed. This core 24 can be a continuous tubular plastic extrusion, a wire of a metal with a high strain hardening coefficient, or a wire of such a metal coated with an extruded polymer. The function of the core 24 depends on its ability, after the catheter structure has been fabricated over it, to reduce in diameter to enable its easy removal from what becomes the lumen of the finished catheter 10. In the case of a tubular plastic core 24, exposure to heat allows the plastic tube to shrink away from the inside of the catheter 10. Metals with high strain hardening coefficients can be stretched by as much as 50% with concomitant diameter reduction. If a neck begins to form, the metal is strain hardened locally there and the necking stops. Annealed austenitic stainless steels, copper and brass work well. If the internal diameter is so large as to require prohibitively stiff metal cores, a core 24 having a central metal wire built to the required diameter with a plastic coating can be used, affording higher dimensional precision and tensile modulus than a tubular plastic core, yet, upon removal of the central wire, with similar behavior.

It will be apparent to those skilled in the art that realizing all of the advantages of the current invention does not depend upon whether the reinforcing coil is encapsulated between two tubular layers (not shown) or is placed within the I.D. of a single, outer tubular layer 12. If an inner tubular layer is desired, a coating can be applied to the core 24 as needed to endow it with the required release properties. The inner tubular layer, if desired, can then be applied to the coated core 24, for example, by sleeving overextrusion or by die coating with a solvent based reactive or prepolymerized material.

Multifilar reinforcing coils 14 can be easily wound onto the core 24, with or without an inner tubular layer, using various devices known in the art, including modified braiding machines and tubular stranders. Passing the wound core 24 through an oven after winding can shape-set a monofilament coil without destroying the properties and anisotropy of the monofilament. Alternatively, multifilamentous coils can be stiffened and set by impregnation and curing or fusion. Finally, the outer tubular layer 12 can be applied by extrusion or die coating.

The best material from which to wind the reinforcing coils are uniaxially oriented flat monofilaments melt spun from polyethylene terephthalate (PET), polybutylene terephthalate (PBT), polypropylene, nylon, Vectran—a liquid crystalline aromatic polyester, or wires of various titanium alloys, nickel titanium alloys, martensitic stainless steels, precipitation hardenable stainless steels, or fibrous or preformed austenitic stainless steel. Alternatively, reinforcing ribbons can be produced by narrow slitting of extruded films of the above organic materials, through these films have longitudinal properties inferior to those of the above monofilaments due to substantially lower shear orientation during and after extrusion. They also have higher transverse properties which can increase coil stiffness. Multifilamentous ribbons, which require either impregnation by a binder or, for some materials, fusion to develop stiffness, can be wound with polyester yarns, Vectran, polyaramids (e.g. Kevlar and Nomex), oriented UHMW polyethylene (e.g. Spectra or Surtran), acrylic and modacrylic fibers, or even stainless steel or fiberglass yarns, pure or plied with a polymeric yarn. Various natural fibers including cotton, wool, silk, or flax would also serve, though they have little to offer over synthetic yarns.

The reinforcing coils can be encapsulated between inner and outer tubular layers which are either "window-bound" to each other through gaps between turns of the reinforcing coil 14 or, with suitable surface treatment or primer coats applied to the reinforcing coil material, the inner and/or outer films can both be "wall-bound" to the coils 14. Given that it is generally desirable to minimize overall wall thickness and that polymeric reinforcing coils 14 must be somewhat thicker than coils would need to be, any inner film must be extremely thin in this case and therefore attached to either the coils 14 or the outer tubular layer 12 to assure catheter patency.

Alternatively, the catheter 10 can be created by merely depositing an outer tubular layer 12 over the reinforcing coils 14. Adhesion between the coils 14 and tubular coating 12, if desired, can be implemented through various methods known in the art including, either alone or in combination, application of chemical primer to the coil 14, various plasma or corona discharge pretreatments of the coil 14 and the application of a reactive binding agent or merely fusible binding agent to coil 14 prior to applying the extruded coating 12. Though not needed to assure kink resistance when the reinforcing coils are relatively stiff and/or wound with small or zero gap, adhesion between coil 14 and coating 12 is highly desirable when the cross-section of the reinforcement is less substantial and wound with a significant space between coils. It further prevents migration of the coil(s) from within the catheter and contributes to their cooperative action.

Materials from which to form the tubular layer(s) are elastomers having flexural moduli between 2 and 170 Mpa (250–25,000 psi)(40 Shore A to 55 Shore D), ideally between 17 and 70 Mpa (2,500–10,000 psi) (80–95 Shore A) and include silicones, polyether block amide resins, polyurethanes, plasticized polyvinylchlorides, some melt processable fluoropolymers, polyester elastomers (e.g. Hytrel), styrenic block copolymers, ionomers, acrylic elastomers, and polyolefin elastomers, including newly developed metallocene catalyzed materials. Because the strong, low LR coils 14 provide longitudinal strength, the tensile strength of the coating material 12 is far less important than in catheters of the prior art.

Additional wound layers can enable the catheter to withstand high injection pressures needed for greater flow rates. To prevent the ballooning of the outer tubular layer in the absence of either strong adhesion to coil(s) 14 or to an inner tubular layer within the coils, the outer tubular layer itself can be constructed of three thinner layers: a medial and outermost elastomeric film with an additional intermediate winding of thin, high modulus mono or multifilament.

If the catheter requires regional stiffness, such can be provided by wrapping an additional unifilar or multifilar coil around the helical reinforcement prior to applying the outer tubular layer. This additional coil comprises at least one thin monofilament or slit film with a heat activated bond-coat applied to at least one surface thereof. When such an adherable film is wrapped in the opposite helical sense immediately atop the first helical reinforcement 14, stiffness can be generated locally by activating the bond-coat. Stiffness is developed only in those treated regions, where the "stiffening wrap" is bound to coil(s) 14 as it crosses each adjacent turn thereof. The "stiffening wrap" thereby serves to stitch across the turns of the first coil in the region where the bond-coat has been thermally activated, so stiffening the catheter there into effectively a perforated, yet still stiff tube formed from the fusion of two opposite winds.

Figure 6:
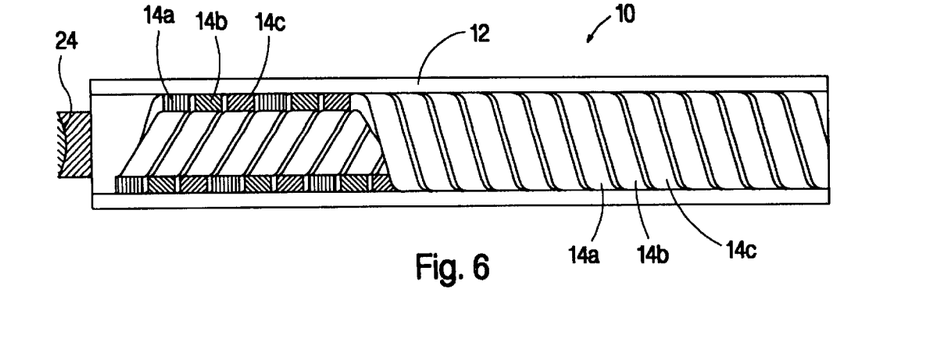
FIG. 6 is a side view of the catheter of the invention shown about a removable core with the reinforcing coils partially cut away and FIG. 7 depicts a preferred embodiment for a reinforced epidural catheter.
Figure 7:
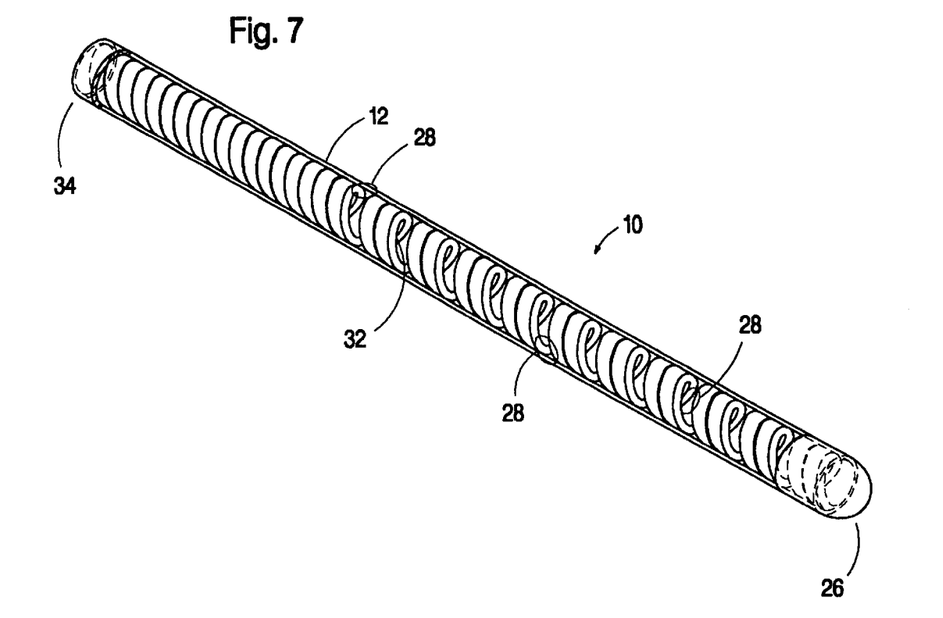

An example of a design for a 19 ga. epidural catheter in accordance with the invention is shown in FIGS. 6 and 7. Three flat, uniaxially oriented polyester monofilaments (14a, 14b, 14c), one of which contains approximately 10% by volume fine tungsten powder (1 micron average particle size), are wound with a pitch of 0.9 mm (0.036") tightly around a core of 0.5 mm (0.020") diameter annealed silver plated copper wire with essentially no winding gap between the 0.125×0.250 mm (0.005"×0.010") monofilaments. Such polyester monofilaments can achieve strengths in excess of five (5) grams per denier (gpd), nearly 760 Mpa (110,000 psi), resulting in each monofilament having a tensile strength exceeding four (4) pounds force. This results in a remarkable smooth, transparent coil 14 which, after passing through an oven at about 170 degrees C. in 10 seconds, can be corona discharge treated and semi-pressure extrusion coated to a final O.D. of 0.98 mm (0.039") with an outer tubular layer 12 of 95 Shore A Tecothane, an aromatic polyurethane with an ultimate strain approaching five (5) available from Thermedics Inc., Woburn, Mass. A radioopaque stripe of tungsten filled polyurethane running the length of the catheter is an alternative method of aiding radiographic visualization of the catheter in vivo. Simply stretching the wound and coated core 24 by about 5–10% results in sufficient core diameter reduction to allow its easy removal from great lengths of catheter blank. These catheter blanks, after core removal, return almost completely to their initial length. Mechanically isolating a small 4 cm section at the distal end and warming this section allows stress relaxation to occur there. When the stretched core and catheter are cut from between the stretching clamps, the core has been plastically elongated and straightened. The region of the catheter not exposed to heat will return to within about 0.5% of its initial length, while the heated region will have permanently elongated. The small 5% gap introduced between turns of coil 14 there, along with the slight reduction in overall diameter (see FIG. 5) and wall thinning that accompanies this stretching greatly increases the flexibility of the distal end of the catheter. A separate, removable 0.010" diameter stainless steel stylet provides sufficient column strength for catheter insertion. FIG. 7 shows the catheter blank with the distal end 26 occluded by UV curable material such as Loctite 3321 after one of the three polyester monofilaments 14a, 14b, 14c has been removed from the distal 10 mm and three openings 28 of 0.35 mm (0.014") diameter are placed through wall, 12 within the helical space vacated by the removed monofilament to allow medication to exit from the internal lumen 32 which is defined between the catheter's proximal end 34 and these openings 28.

Figure 8:
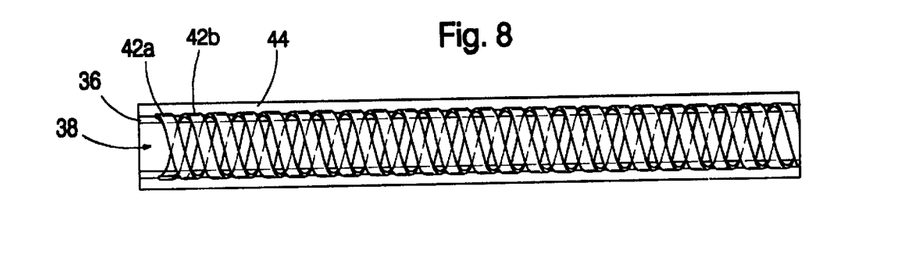
FIG. 8 depicts a reinforced PICC catheter in accordance with the present invention.

A preferred embodiment of a 2 French PICC catheter is shown in FIG. 8. A 0.05 mm (0.002") thick inner tubular layer 36 is deposited onto a 0.4 mm (0.016") diameter annealed stainless steel wire 38 which has been dispersion coated with PTFE 40 for release. The inner tubular layer 36 can be formed either from 70 Shore A silicone or from 85 Shore A polyurethane sleeved on by extrusion. Hereupon, two separate leads of 25–75 denier polyethylene terephthalate monofilament, calendered Vectran monofilament, or Vectran multifilament yarn are wound with a 0.5 mm (0.020") pitch, 42a, 42b. After using heat to set the shape of these coils if possible, an 0.075 mm (0.003") thick outer tubular layer 44 of similar composition as 36 is applied to build the catheter to an O.D. of 0.65 mm (0.026"). Achieving good adhesion to the inner tubular layer 36 through the interstices of the double lead coil is important for catheter integrity and fatigue strength.

The present invention has been shown and described in what are considered to be the most practical and preferred embodiments. It is anticipated, however, that departures may be made therefrom and that obvious modifications will be implemented by persons skilled in the art.

I claim:

1. A catheter reinforced to prevent luminal collapse and tensile failure comprising:

(a) a longitudinally elongated tubular member comprising an outer cover, a proximal end, and a distal end with at least one lumen defined therethrough, (b) at least one orifice positioned near the distal end of the tubular member, defined in at least one of said distal end and said elongated tubular member proximal to said distal end thereof for enabling fluid flow through the catheter, and (c) at least one predominantly non-metallic helical reinforcing member wound around the longitudinal axis of said elongated tubular member for reinforcing said tubular member to prevent radial collapse of said tubular member during bending and pinching thereof and to prevent longitudinal breakage of said tubular member under tension, said reinforcing member having a winding gap, a wound length, and an unwound length, and a length ratio defined by the unwound length of said reinforcing member relative to the wound length of said member, (d) said helical reinforcing member having a length ratio less than the approximate ultimate strain of the outer cover plus 1.

2. The catheter in accordance with claim 1, wherein the length ratio is between 2 and 3.

3. The catheter in accordance with claim 1, wherein the length ratio is less than 7.

4. The catheter in accordance with claim 1 wherein said helical reinforcing member is wound from materials including polyethylene terephthalate, polybutylene terephthalate, polypropylene, nylon and liquid crystalline aromatic polyester.

5. The catheter in accordance with claim 4, wherein said helical reinforcing member is wound from uniaxially oriented flat monofilament.

6. The catheter in accordance with claim 4, wherein said helical reinforcing member is approximately 4–5 mils thick and approximately 9–12 mils wide.

7. The catheter in accordance with claim 4, wherein said winding gap is greater along the distal end of the tubular member than along the proximal end of the tubular member.

8. The catheter in accordance with claim 7, wherein said orifice is disposed between a winding gap along the distal end of the tubular member.

9. The catheter in accordance with claim 4 comprising a plurality of parallel helical reinforcing members wound at a common diameter.

10. The catheter in accordance with claim 9, wherein the composite gap between adjacent reinforcing members is greater near the distal end of the tubular member than along the proximal end of the tubular member by virtue of the removal of at least one of the helical reinforcing members near said distal end.

11. The catheter in accordance with claim 10, wherein a plurality of orifices are disposed within said winding gaps near the distal end of the tubular member.

12. The catheter in accordance with claim 4, further comprising an occluded distal end.

13. A catheter reinforced to prevent luminal collapse and tensile failure comprising:

(a) a longitudinally elongated tubular member comprising an outer tubular cover, an inner tubular layer, and a proximal end, with at least one lumen defined therethrough, (b) at least one orifice positioned near the distal end of the tubular member defined in at least one of said distal end and said elongated tubular member proximal to said distal end thereof for enabling fluid flow through the catheter, and (c) at least one, predominantly non-metallic helical reinforcing member wound around the longitudinal axis of said elongated tubular member between said inner tubular layer and outer tubular cover, for reinforcing said tubular member to prevent radial collapse of said tubular member during bending and pinching thereof and to prevent longitudinal breakage of said tubular member under tension, said reinforcing member having a winding gap, a wound length, and an unwound length and a length ratio defined by the unwound length of said reinforcing member relative to the wound length of said member, (d) said helical reinforcing member having a length ratio less than the ultimate strain of the outer tubular cover plus 1.

14. The catheter in accordance with claim 13, wherein the length ratio is between 2 and 3.

15. The catheter in accordance with claim 14 comprising at least two helical reinforcing members.

16. The catheter in accordance with claim 15, wherein at least one of said helical reinforcing members is provided with X-ray opacity means.

17. A catheter reinforced to prevent luminal collapse and tensile failure comprising:

(a) a longitudinally elongated tubular member comprising an outer cover, a proximal end and an occluded tip distal end, with at least one lumen defined therethrough, (b) a plurality of orifices positioned along the outer cover near the distal end of the tubular member for enabling fluid flow between said proximal end and said near distal end through the outer cover, and (c) a plurality of helical reinforcing members wound around the longitudinal axis of said elongated tubular member for reinforcing said tubular member to prevent radial collapse of said tubular member during bending and pinching thereof and to prevent longitudinal breakage of said tubular member under tension, said plurality of reinforcing members having a composite winding gap, a wound length, and an unwound length, and each of said reinforcing members having a length ratio defined by the unwound length of a reinforcing member relative to the wound length of said member, (d) said helical reinforcing members having a length ratio less than the ultimate strain of the outer tubular cover plus 1.

18. A catheter in accordance with claim 17 having a length ratio between 2 and 3.

19. A catheter in accordance with claim 18, wherein at least one of said helical reinforcing members is removed from a portion of said elongated tubular member proximal to said distal end thereby increasing the composite gap of said helical reinforcing members, such that at least one orifice is defined through such increased composite gap.

\* \* \* \* \*